United States Patent [19]

Talcott

[11] 4,082,509

[45] Apr. 4, 1978

[54] METHOD OF STORING BLOOD AND A BLOOD STORAGE BAG THEREFOR

[75] Inventor: Thomas D. Talcott, Santa Barbara, Calif.

[73] Assignee: Dow Corning Corporation, Midland, Mich.

[21] Appl. No.: 712,106

[22] Filed: Aug. 5, 1976

[51] Int. Cl.² ............... A61L 13/00; A61M 1/02; A61M 1/03; A61M 5/14
[52] U.S. Cl. ............... 21/58; 23/258.5 R; 128/214 D; 128/272; 195/1.8
[58] Field of Search ......... 128/214 D, 272, DIG. 24; 424/101; 195/1.8; 23/258.5 R; 21/2, 58

[56] References Cited

U.S. PATENT DOCUMENTS

| | | | |
|---|---|---|---|
| Re. 25,129 | 2/1962 | Walter | 23/258.5 R |
| 2,301,710 | 11/1942 | Scudder | 23/258.5 R UX |
| 3,291,612 | 12/1966 | Schneider et al. | 424/101 X |
| 3,418,209 | 12/1968 | Ushakoff | 23/258.5 R X |
| 3,579,999 | 5/1971 | Schwartz | 424/101 X |
| 3,677,022 | 7/1972 | Schwartz | 424/101 X |
| 3,729,947 | 5/1973 | Higuchi | 424/101 X |
| 3,874,384 | 4/1975 | Deindoerfer et al. | 128/272 |
| 3,925,153 | 12/1975 | Laborit | 195/1.8 |
| 3,942,529 | 3/1976 | Waage | 128/214 D |

FOREIGN PATENT DOCUMENTS

| | | | |
|---|---|---|---|
| 459,951 | 1/1937 | United Kingdom | 424/101 |
| 901,675 | 7/1962 | United Kingdom | 424/101 |

OTHER PUBLICATIONS

Beutler et al.; Preservation of Red Cell 2,3 DPG and Viability in Bicarbonate-Containing Medium: The Effect of Blood Bag Permeability, J. Lab. Med., Nov. 1972, pp. 723-728.

Primary Examiner—Morris O. Wolk
Assistant Examiner—Michael S. Marcus
Attorney, Agent, or Firm—Robert L. McKellar

[57] ABSTRACT

A method of storing blood in which a plastic blood collection bag is further supplied with silicone rubber into which pure $Ca(OH)_2$ has been compounded to prolong the useful life of blood, especially the erythrocytes, since their viability can be enhanced by removal of $CO_2$ from the blood. Such removal can maintain an adequate pH balance in the complex blood system which appears to be essential to maintaining the blood in storage for prolonged periods of time.

3 Claims, No Drawings

METHOD OF STORING BLOOD AND A BLOOD STORAGE BAG THEREFOR

BACKGROUND OF THE INVENTION

The anatomy and physiology of blood has been of great interest to the human race for a long time, because, as recognized centuries ago, the blood system is the fluid pipeline that maintains the complex chemical balance of the human body. The blood system carries nutrients to the other living tissues of the body and at the same time carries away the waste by-products of the multitudinous complex chemical reactions that are going on inside the body and which are essential to life itself.

Severe intrusions on body tissues and/or the blood system itself often requires the supplementation of blood to the blood system. Generally, if the intrusion is not too severe or the loss of blood is not too copious, the body has a unique system for supplementing or replacing lost blood.

In those instances when the body cannot replace or supplement the needed blood because of sheer volume loss or because the body has a physiological malfunction, the replacement or supplementation can come from an external source, such as stored blood.

Historically, the storage of blood outside the body is not very old. With the onset of the Second World War, the need for large volumes of replacement blood brought on a flurry of activity in researching the best methods of storing blood.

Since the end of the Second World War and up to approximately the beginning of the present decade, the systems for storing blood that were developed were those used during the war period. At the very best, however, the duration of storage of whole blood in its liquid form, was 21 days.

Such storage systems usually involved the storage of blood in an Acid Citrate-Dextrose solution.

Recently, Dr. Lee Wood and Dr. Ernest Beutler in a publication, Transfusion, Vol. 11, No. 3, May-June, 1971, pp. 123–133, reported that blood could be stored for 35 days by the co-use of adenine with Acid Citrate-Dextrose solutions and that such a practice was the primary storage system in Sweden.

They further set forth a method they had developed for the storage of erythrocytes. They remove the plasma from whole blood and store the erythrocytes in an artificial media. Their work shows that they can get equivalent storage to the ACD-adenine storage system.

One of the major problems in the storage of whole blood is that the erythrocytes produce large quantities of lactic acid from glucose. This phenomena proceeds even when the blood is stored at low temperatures. The presence of the lactic acid, among other things, contributes to the continued decrease in the pH of the stored whole blood.

The lowering of the blood pH has a dramatic effect on the viability of the erythrocytes when the blood is transfused.

The mechanisms involved in the effect are described by Wood and Beutler in an article entitled "Preservation of Red Cell 2, 3-DPG and Viability in Bicarbonate-Containing Medium: The Effect of Blood Bag Permeability", Journal of Lab and Clinical Medicine, Vol. 80, No. 5, p.p. 723–728, "The fall in the pH of the stored cells results initially in the loss of their 2,3-diphosphoglycerate (2,3-DPG), so necessary for efficient delivery of oxygen to the tissues. Eventually, glycolysis is choked off at the pH-sensitive hexokinase and phosphofructokinase steps, so that the erythrocyte loses its capacity to live and circulate when transfused. Thus, regulation of pH plays a key role in liquid preservation".

Wood and Beutler go on to state the essential problem, "the use of very alkaline blood perservative solutions is unsatisfactory, however. Very high pH levels result in reduction of NAD to NADH in the lactate-pyrovate system, and thus impede glycolysis at the glyceraldehyde phosphate dehydrogenose step. Although alkaline preservatives result in good 2,3-DPG maintenance, adenosinetriphosphate (ATP) is rapidly depleted under these conditions, and viability is poor. To some extent, this effect may be counteracted by the addition of pyrovate to reoxidize NADH, but even very alkaline preservatives cannot absorb enough hydrogen ions to maintain the pH level above the critical values required to prevent the decomposition of 2,3-DPG.

Clearly, it would be helpful to have a highly efficient buffer system which would maintain the pH of preserved cells above 7.4 in the face of the production of large amounts of lactic acid. Yet, no buffer ion which can absorb this large amount of acid and yet be reinfused is known".

Prior art attempts at preventing degeneration of whole blood suffering from the disadvantages described above, that is, generally the buffer solutions of sufficient strength required to maintain the high pH level have the disadvantage of not being compatible enough to reinfuse in the human without deleterious side effects. Further, attempts have been made to include small pouches, containing a $CO_2$ absorbent, inside the larger storage bag but this method is highly dependent on the ability of $CO_2$ to penetrate the small bag to reach the absorbent and further, these small bags are readily susceptible to a mucous-like build-up on their surface which further cuts down on the transmission of $CO_2$ to the contained absorbent.

Moreover, the small bags containing the $CO_2$ absorbent have the possibility of highly contaminating the whole blood if they leak or are ruptured in some manner.

Further, such a bag-within-a-bag design causes complicated fabrication problems for the bag manufacturer.

SUMMARY OF PRESENT INVENTION

The present invention is directed to overcoming some of the problems associated with blood storage.

It is an object of the present invention to provide a method of prolonging the period of storage of blood.

It is another object of the present invention to prolong the storage of blood yet provide for wholesome blood that can be reinfused.

It is yet another object of this invention to provide a composition which can be used in a whole blood storage bag to prolong the life of the whole blood stored therein.

It is still another object of this invention to provide a method of easier fabrication of a blood storage bag containing compositions which will prolong the life of the blood stored therein.

It is a further object of this invention to provide a blood storage bag which can prolong the life of whole blood and which can contribute little or no whole blood contamination from the inventive composition.

There is, therefore, provided by this invention a composition of matter to be used in blood storage bags to inhibit the degeneration of the blood stored therein.

Such a composition consists of a curable silicone rubber containing compounded therein essentially pure $Ca(OH)_2$ as a $CO_2$ absorbent.

For purposes of this invention, "essentially pure" means that the $Ca(OH)_2$ useful in the invention contains at least 95% of $Ca(OH)_2$ as opposed to CaO. Further, "essentially pure" also preferably refers to the highest grade of $Ca(OH)_2$ commercially available wherein the other impurities present are non-calcium materials and are present in very minute quantities, i.e., on the order of parts per million.

There is also provided a method of storing blood and a blood storage system aimed at retarding degeneration of blood which consists of equipping a blood storage bag with the above mentioned compounded rubber in the form of sheets, ribbons, kernels, granules, lumps or small blocks. By equipping is meant that the compounded silicone rubber is added to a blood storage bag along with the normal artificial medias. Such compounded silicone rubber thus acts as a $CO_2$ sink and thereby facilitates the inhibition of the degeneration of the whole blood stored therein.

DETAILED DESCRIPTION

The present invention contemplates contacting blood with cured silicone rubber containing essentially pure $Ca(OH)_2$ while the blood is stored. It should be understood for purposes of this invention, that because the compounded rubber acts as a $CO_2$ sink, the surface area of the silicone rubber is an important factor in the selection of the physical form of the rubber to be used. To provide the necessary surface area the rubber is in the form of sheets, ribbons, kernels, granules, lumps or small blocks, but some degree of care is necessary in choice of configurations. For example, if granules are used to provide a large surface area for absorption of large quantities of $CO_2$, care must be taken that the granules are not so small as to clog the infusion tubes and etc., of the storage bag. On the other hand, very large blocks or spheres of such rubber do not allow the requisite surface area for enough $CO_2$ absorption. Thus, design of the silicone pieces actually used is dependent on the amount of $CO_2$ absorption that is actually desired and this has to be balanced against possible mechanical malfunctions such as the clogging described above.

The silicone rubbers useful in this invention are those silicone rubbers which are easily curable. Such methods of curing are preferably peroxide cures or platinum catalyzed curing of $\equiv$SiH containing siloxanes with $\equiv$Si alkenyl containing siloxanes.

Such silicone rubbers are well known in the art and further elaboration is not required herein.

The $Ca(OH)_2$ useful in this invention is $Ca(OH)_2$ that is essentially pure. For obvious reasons, poorer grades of $Ca(OH)_2$ should not be used because of the possible contamination problems. Preferably, $Ca(OH)_2$ is used that has greater than 95% $Ca(OH)_2$ as opposed to CaO. Further, preferably there should be used a $Ca(OH)_2$ that is the purest that can be reasonably obtained and which has impurities other than calcium in the parts per million range.

The $Ca(OH)_2$ is compounded into the uncured silicone rubber by any means normally used in the art such as a two-roll mill.

The largest amount of $Ca(OH)_2$ that can be used is limited by the amount that can be milled into silicone rubber without detracting from the cure or the physical properties of the silicone rubber. The smallest amount is determined by the practical effects of absorbing power and quantities of $CO_2$ that are required to be absorbed. Usually, the amount ranges from 5–30 parts based on 100 parts of the silicone rubber. The compounded rubber is then cured by any convenient means which is conventional in the art and which is dependent on the cure system used and the catalyst required.

The uncured rubber can be molded to the proper shape or can be molded in blocks or sheets and cut or carved to the proper physical form.

At the present time, the preferred form both from a functional surface area and from a physical malfunctions aspect, is a 3 cm × 3 cm piece that is 1 cm thick and which has the corners slightly rounded.

The pieces are simply inserted into a blood storage bag during the fabrication of the bag and are allowed to float free within the bag.

The silicone rubber pieces adapt very nicely to sterilization techniques.

Now so that those skilled in the art can more fully understand the invention, the following example is submitted.

EXAMPLE

Silicone rubber into which 17% by weight of pure $Ca(OH)_2$ had been compounded and which had been cured were fashioned into 3.0 cm × 3.0 cm × 1 cm blocks.

One block was inserted into each blood collection bag for this example by opening the bottom of an empty 600 ml transfer pack (Fenwal PL 130 plastic), inserting the block and then resealing the pack with a hot iron and autoclaving for 20 minutes at 121° C.

Four hundred and fifty ml of blood were collected from healty adult donors into 67.5 ml of ACD (NIH formula A). The blood was allowed to stand for 15–30 minutes at room temperature, and then was centrifuged at 4° C at 4500 x g for 5 to 10 minutes in a Sorvall RC-3 centrifuge with a swinging bucket rotor. The plasma and buffy coat were both pressed off, and 200 ml of preservative solution (BAGPM) containing 101.4 mM of sodium bicarbonate ($NaHCO_3$), 14.3 mM sodium carbonate ($Na_2CO_3$), 1 mM bisodium phosphate ($Na_2HPO_4$), 1 mM adenine, 55 mM glucose and 0.5% mannitol was added for each volume of plasma expressed. After gentle but thorough mixing, the red cell suspension was aseptically transferred into the bag containing the blocks. The red cells were then stored at 4° C for 42 days, and agitated for 1 minute either once at the time of sampling, or five times weekly to ensure thorough mixing.

Erythrocyte ATP was quantitated by the hexokinase method (set out in Beutler, E., "Red Cell Metabolism", A Manual of Biochemical Methods, Second Edition, New York, 1975, Greene and Stratton), and the concentration of 2,3-DPG was measured by a modification of the technique of Krimsky. (see Beutler, E. immediately above.) The pH was determined by a technique which allowed anaerobic measurements at 0°–4° C. (Bensinger, T.A., Metro, J. and Beutler, E., redesigned apparatus for anaerobic measurement of blood pH at low temperatures, Amer., J. Clin. Path., 63, 264–268, 1975.)

Four units of blood were stored in BAGPM with the blocks and agitated one time per week. The pH ranged from a high of 7.82 ± .02 on day 7 to 7.41 ± .03 on day 42. Seven units containing the BAGPM and blocks were agitated five times weekly and these units maintained their pH at 7.86 ± .03 on day zero to 7.55 ± .08 on day 42.

Intracellular 2,3-DPG which was 13.16 ± .88 μMole/g Hgb on day zero was 10.22 ± 2.35 μMole/g Hgb on day 42 in the units stored with BAGPM and blocks that were agitated five times weekly. 2,3-DPG, which was originally 15.3 ± 1.6 μMole/g at the time of drawing, was 10.13 ± 1.20 μMole/g Hgb on day 42 if the system was agitated once weekly. In the units agitated once weekly, the day 42 ATP was 2.40 ± 0.64 μMole/g Hgb. The blood agitated five times weekly was 2.40 ± 0.64 μMole/g Hgb. The blood agitated five times weekly had ATP levels of 1.88 ± 0.26 μMole/g Hgb after 42 days of storage.

That which is claimed is:

1. A method of storing blood which comprises
compounding a curable silicone rubber with Ca(OH)$_2$ which is to preserve and extend the storage life of whole blood;
inserting the compounded silicone rubber into a blood storage bag;
subsequently infusing the bag with whole blood,
whereupon there is obtained a storage stable blood.

2. A method of storing blood which comprises
compounding a curable silicone rubber with Ca(OH)$_2$ which is to preserve and extend the storage life of whole blood;
inserting the compounded silicone rubber into a blood storage bag containing an artificial blood storage media;
subsequently infusing the bag with blood,
whereupon there is obtained a storage stable blood.

3. A method of storing blood as claimed in claim 1 wherein the silicone rubber is present in a ratio of 100 parts to 5–30 parts of Ca(OH)$_2$.

* * * * *